(12) United States Patent
Müller et al.

(10) Patent No.: US 9,278,906 B2
(45) Date of Patent: Mar. 8, 2016

(54) PROCESS FOR HYDROGENATING AROMATIC DI- AND POLYAMINES TO CYCLOALIPHATIC DI- AND POLYAMINES

(71) Applicant: Bayer MaterialScience AG, Leverkusen (DE)

(72) Inventors: Thomas E. Müller, Aachen (DE); Christoph Gürtler, Köln (DE); Reinhard Halpaap, Odenthal (DE); Ewa Gebauer-Henke, Aachen (DE); Walter Leitner, Aachen (DE); Patrick Tomkins, Erkelenz (DE); Christoph Thiebes, Köln (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 14/614,183

(22) Filed: Feb. 4, 2015

(65) Prior Publication Data

US 2015/0218083 A1    Aug. 6, 2015

(30) Foreign Application Priority Data

Feb. 5, 2014  (EP) .................................... 14153937

(51) Int. Cl.
  *C07C 209/72*  (2006.01)
(52) U.S. Cl.
  CPC ........... *C07C 209/72* (2013.01); *C07C 2101/14* (2013.01)
(58) Field of Classification Search
  CPC ............................. C07C 209/72; B01J 23/464
  See application file for complete search history.

(56) References Cited

U.S. PATENT DOCUMENTS

| | | | |
|---|---|---|---|
| 4,448,995 A * | 5/1984 | Allen ............................ | 564/451 |
| 5,214,212 A * | 5/1993 | Whitman ...................... | 564/451 |
| 5,360,934 A * | 11/1994 | Vedage et al. ................ | 564/451 |
| 5,516,935 A | 5/1996 | Bischof et al. | |
| 6,075,167 A | 6/2000 | Kim et al. | |
| 2010/0292510 A1 | 11/2010 | Pfeffinger et al. | |
| 2012/0226017 A1* | 9/2012 | Pfeffinger et al. ............ | 528/405 |

FOREIGN PATENT DOCUMENTS

| | | |
|---|---|---|
| EP | 0630882 A1 | 12/1994 |
| EP | 1078918 A1 | 2/2001 |

OTHER PUBLICATIONS

Kim et al., "Ru-Catalyzed Hydrogenation of Aromatic Diamines: The Effect of Alkali Metal Salts", *J. Mol. Catal. A: Chem.*, vol. 132, pp. 267-276 (1998).
Gebauer-Henke et al., "Nitro Promoters for Selectivity Control in the Core Hydrogenation of Toluidines: Controlling Adsorption on Catalyst Surfaces", *Chemcatchem*, vol. 6, pp. 2910-2917 (Sep. 12, 2014).
European Search Report for EP Application No. 15153576.2 dated Jul. 3, 2015.

* cited by examiner

*Primary Examiner* — Sudhakar Katakam
(74) *Attorney, Agent, or Firm* — Drinker Biddle & Reath LLP

(57) ABSTRACT

A process for hydrogenating aromatic di- and polyamines is provided comprising the steps of reacting the aromatic amine with hydrogen in the presence of a catalytic system, wherein the catalytic system comprises a heterogeneous catalyst comprising a metal selected from the group consisting of Cr, Mo, W, Mn, Re, Fe, Ru, Os, Co, Rh, Ir, Ni, Pd and/or Pt and a support, and wherein the catalyst system further comprises an organic nitro compound. Hydrogenation of aromatic di- and polyamines having two or more amino groups bound to the aromatic ring produces cycloaliphatic di- and polyamines, which are useful chemical intermediates, e.g., for further reaction with epoxides or isocyanates. The amino groups may also be converted to isocyanates via reaction with phosgene. The resulting cycloaliphatic di- and polyisocyanates may also be used as monomers for making polymers.

14 Claims, No Drawings

PROCESS FOR HYDROGENATING AROMATIC DI- AND POLYAMINES TO CYCLOALIPHATIC DI- AND POLYAMINES

This application claims the benefit of European Patent Application 14153937.9 filed Feb. 5, 2014, the entire disclosure of which is incorporated herein by reference.

FIELD OF THE INVENTION

The present invention relates to a catalytic process for hydrogenating aromatic amines with the aid of a selected catalyst system.

BACKGROUND OF THE INVENTION

Hydrogenation of aromatic rings having two or more amino groups bound to the aromatic ring produces amino-substituted hydrogenated rings, such as cycloaliphatic di- or polyamines, which are useful chemical intermediates, e.g., for further reaction with epoxides or isocyanates. The amino groups may also be converted to isocyanate groups e.g. via reaction with phosgene or through known phosgene free methods. The resulting cycloaliphatic di- or higher functional isocyanates may also be used as monomers for making polymers, in particular, polyurethanes.

Until now, many polyurethane materials are made based on aromatic di- and polyamines as starting materials. A disadvantage of using aromatic di- and polyamines is that the amines, the corresponding aromatic di- and polyisocyanates and the resulting products darken with time and gradually turn brown or black e.g. due to oxidation upon contact with air. Products derived from aliphatic and/or cycloaliphatic isocyanates behave differently and are known as "light stable" after conversion to polyisocyanates or polyurethanes. The stability of compounds derived from di- and polyamines may be improved by hydrogenating the aromatic ring to the corresponding cycloaliphatic di- and polyamines. Known heterogeneous hydrogenation catalysts, however, lack in sufficient activity for the core-hydrogenation of amino-substituted aromatic rings and lack in chemoselectivity towards primary amines. Frequently observed side reactions include the condensation of primary amino groups to secondary or tertiary amino groups and/or the hydrogenolytic cleavage of the C—N bond between the aromatic ring and the amino group.

Moreover, many applications of di- and polyamines, such as for making active ingredients in the pharmaceutical industry or use as a monomer for making polymers, require a high degree of stereomeric selectivity with regard to the position of the substituents relative to each other on the hydrogenated ring, such as the resulting cycloaliphatic ring. When incorporated into a polymer chain, e.g., by conversion to the corresponding diisocyanate and subsequent reaction with a diol, trans-1,4-diaminocyclohexane results in a polymer chain with linear connections, while cis-1,4-diaminocyclohexane results in a polymer chain with non-linear connections. Materials made from polymers with such linear or non-linear connections display different macroscopic properties, such as a different glass transition temperature. The properties of materials made from diastereomeric mixtures of 1,4-diaminocyclohexanes vary in their properties with the content of the different diastereomers. Therefore, control of the ratio of the diastereomers is essential for controlling the properties of such materials. Diastereomers also may have different reactivities, so that compositions having a high proportion of one diastereomer can improve the uniformity of reaction rates when used in subsequent reactions, such as polyaddition or phosgenation reactions.

1,2-Diaminocyclohexanes with two amino groups attached to the same cycloaliphatic ring system in the 1,2-positions, as represented by formulas (I), which contain a high proportion of amino groups in cis position to each other, are advantageous for the reaction with phosgene. This is because the cis isomers are less prone than the trans isomers to form cyclic urea compounds, which are undesired by-products in the synthesis of isocyanates.

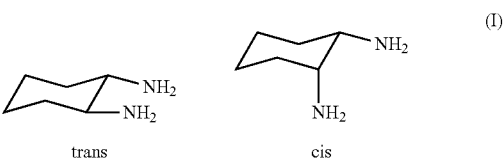 [SMILES: NC1CCCCC1N ; NC1CCCCC1N]

1,3-Diaminocyclohexanes with two amino groups attached to the same cycloaliphatic ring system in the 1,3-positions, as represented by formulas (II), which contain a high proportion of amino groups in trans position to each other are advantageous for the reaction with phosgene. This is because the trans isomers cannot form cyclic urea compounds, which are undesired by-products in the synthesis of isocyanates.

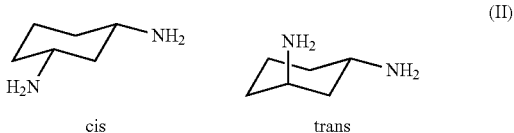 [SMILES: NC1CCCC(N)C1 ; NC1CCCC(N)C1]

1,4-Diaminocyclohexanes with the two amino groups attached to the same cycloaliphatic ring system in the 1,4-positions, as represented by formulas (III), which contain a high proportion of amino groups in trans position to each other are advantageous for the reaction with phosgene. This is because the trans isomers cannot form cyclic urea compounds, which are undesired by-products in the synthesis of isocyanates.

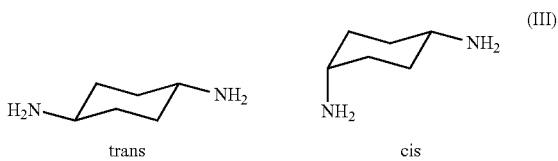 [SMILES: NC1CCC(N)CC1 ; NC1CCC(N)CC1]

Among the methyl substituted 2,4-diaminocyclohexane derivatives represented by formulas (IV) trans-cis-2,4-diamino-1-methyl-cyclohexane and cis-trans-2,4-diamino-1-methyl-cyclohexane, whereby cis and trans each refer to the position of the respective amino group relative to the methyl group, obtained by hydrogenating 2,4-diaminotoluene (2,4-TDA), are particularly advantageous for phosgenation, since these diastereomers do not form cyclic compounds, and trans-trans-2,4-diamino-1-methyl-cyclohexane, another diastereomer obtained by hydrogenating 2,4-TDA, is considered acceptable, since this diastereomer is less prone to form cyclic compounds, while cis-cis-2,4-diamino-1-methyl-cyclohexane is particularly prone to forming cyclic urea compounds during phosgenation.

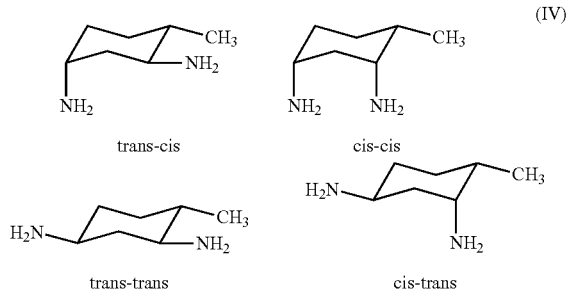

(IV)

trans-cis  cis-cis
trans-trans  cis-trans

Analogously, among the methyl substituted 2,6-diaminocyclohexane derivative as represented by formulas (V), cis-trans-2,6-diamino-1-methyl-cyclohexane, obtained by hydrogenating 2,6-diaminotoluene (2,6-TDA), is particularly advantageous for phosgenation, since this diastereomer does not form cyclic compounds, and trans-trans-2,6-diamino-1-methyl-cyclohexane, another diastereomer obtained by hydrogenating 2,6-TDA, is considered acceptable, since this diastereomer is less prone to form cyclic compounds, while cis-cis-2,6-diamino-1-methyl-cyclohexane is particularly prone to forming cyclic urea compounds during phosgenation.

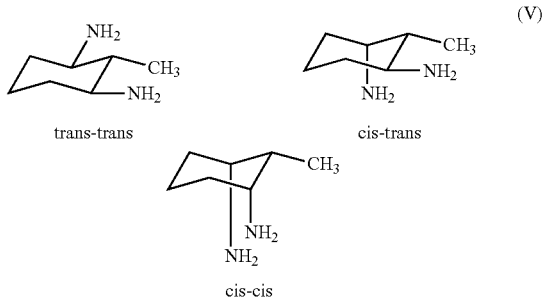

(V)

trans-trans  cis-trans
cis-cis

The phosgenation of such cycloaliphatic 1,2- or 1,3-diamines is known, see EP-B 1078918. Independent from ease of phosgenation, the preferred diastereomers are advantageous for the modification (oligomerisation) of the synthesized diisocyanates.

The use of conventional catalysts for the hydrogenation of 2,4-TDA or 2,6-TDA tends to provide diastereomer mixtures having a high proportion of undesired isomers, such as the cis-cis isomer.

An example of a hydrogenation of aromatic amines is given in EP 0 630 882 A1. Ring hydrogenation is effected by reacting the aromatic amine with $H_2$ in the presence of a catalyst comprising Rh on kappa-alumina. Also claimed is a process for hydrogenating crude methylene-dianiline (MDA) to produce 4,4'-methylene-dicyclohexylamine (PACM) in the presence of a 7:1 mixture of a Rh catalyst and a Ru catalyst, where at least the Rh catalyst is supported on kappa-alumina. The obtained product comprised 1 to 3% deaminated products and 13 to 19% secondary amines. It would be desirable to have access to catalytic systems having a lower rhodium content and displaying a higher reaction rate also for less reactive aromatic amines.

An example of the use of additives in the hydrogenation of aromatic amines is given in Kim et al., J. Mol. Catal. A: Chem. 132 (1998) 267-276. The influence of added alkali metal salts on the performance of ruthenium catalysts has been examined. It was found that the cations of the metal salts interac with the supporting material. $NaOCH(CH_3)_2$ was identified as the active species. The product obtained in the hydrogenation of methylene-dianiline (MDA) and 1,4-phenylenediamine comprised 2 to 99% of products with partially hydrogenated aromatic rings, 1 to 5% deaminated products, as well as 2 to 7% secondary amines. It would be desirable to have access to catalytic systems having an improved reaction rate also for less reactive aromatic amines.

US 2010/292510 A1 relates to a process for preparing cycloaliphatic amines comprising performing hydrogenation of corresponding aromatic compounds with hydrogen-comprising gas at a temperature of from 30 to 280° C. and a pressure of 50-350 bar, in the presence of ruthenium catalysts, and from 1% by weight to 500% by weight, based on the catalyst (calculated as elemental ruthenium (Ru)), of suspended inorganic additives.

U.S. Pat. No. 5,214,212 teaches the addition of metal salts as promoters in a process for hydrogenating aromatic amines. According to the disclosure, the addition of promoters leads to an improvement in the reaction rate and to a reduction in by-product formation. To maintain high activity of the catalyst system in the hydrogenation process, a transition and/or lanthanide metal salt promoter is added to the reaction system in an effective amount to increase the hydrogenation rate, eliminate the induction period of the hydrogenation reaction, and decrease the amount of higher boiling by-products. By way of illustration, an effective amount of the transition or lanthanide metal salt promoter is in the range from about 0.1% to about 15% by weight based on the starting aromatic amine. The preferred range is from about 0.3% to about 10.0%. These metal salt promoters can be used alone or in combination with other additives. Counter-ions such as the sulfate and phosphate can be used because they do not have non-bonded electrons on the sulfur and phosphorus, respectively. Thus, ferrous and cerous sulfates (either as the anhydrous salt or as a hydrate) are illustrative. Other anions that satisfy these criteria such as carboxylates (e.g. acetates) can be used.

U.S. Pat. No. 4,448,995 teaches a process for the catalytic hydrogenation of di(4-aminophenyl)methane to a liquid di(4-aminocyclohexyl)methane containing from 15 to 40% by weight of the trans-trans isomer comprising hydrogenating di(4-aminophenyl)methane at a hydrogen pressure of at least 500 psi and at a temperature of from 100 to 300° C., in the presence of a ruthenium catalyst supported on an inert carrier, said catalyst being moderated with from 65 to 700% by weight, based on the weight of the ruthenium, of a compound selected from the group consisting of nitrates and sulfates of alkali metals and alkaline earth metals. According to one embodiment, the catalyst is moderated with a compound selected from the group consisting of lithium nitrate and magnesium nitrate.

U.S. Pat. No. 6,075,167 relates to a method of preparing cycloaliphatic diamines by hydrogenating an aromatic diamine in an organic solvent in the presence of a supported ruthenium catalyst, wherein a metal nitrite is used as a catalyst promoter. In one embodiment, the metal nitrite is selected from the group consisting of $Ba(NO_2)_2$, $NaNO_2$, $KNO_2$ and $AgNO_2$.

SUMMARY OF THE INVENTION

The present invention has as an object of providing cycloaliphatic di- and polyamines in the hydrogenation of the corresponding aromatic di- and polyamines with a higher catalyst activity compared to the state of the art, in order to shorten the time required for the hydrogenation reaction. A high initial catalyst activity enables achievement of higher conversions, when the reaction is stopped at a certain reaction time characterised by a partial conversion of the aromatic di- and polyamine. Unconverted starting material is separated and recycled. This procedure provides a high space-time yield (optimal utilization of the reactor) as the hydrogenation reaction slows down proportionally, when high conversions are approached. Further, the process for hydrogenating aromatic di- and polyamines provides cycloaliphatic di- and polyamines with high chemoselectivity with respect to the ring hydrogenated product. Further, the cycloaliphatic di- and polyamines obtained are characterised by a sufficiently low content of ring-forming diastereomers, such as the cis-cis isomer in case of 2,6-TDA and/or 2,4-TDA hydrogenation.

According to the present invention, these and other objects are achieved by a process for hydrogenating aromatic di- and polyamines comprising the steps of:
  reacting, in a reactor, at least one aromatic amine with hydrogen in the presence of a catalytic system, wherein the catalytic system comprises at least one heterogeneous catalyst,
  wherein the heterogeneous catalyst comprises a metal selected from the group consisting of Cr, Mo, W, Mn, Re, Fe, Ru, Os, Co, Rh, Ir, Ni, Pd, Pt and combinations thereof, and
  wherein the catalyst system further comprises an organic nitro compound, and
  obtaining a reaction product from the reaction.

In one embodiment of the process of the invention, the aromatic amine is selected from the group consisting of o-, m-, and p-phenylenediamine, 2,3-diaminotoluene, 2,4-diaminotoluene, 2,6-diaminotoluene, 3,4-diaminotoluene, 2,3-diamino-p-xylene, 2,5-diamino-p-xylene, 2,6-diamino-p-xylene, N-methyl-o-phenylenediamine, N-ethyl-o-phenylenediamine, 4-methoxy-m-phenylenediamine, N-methyl-m-phenylenediamine, N-ethyl-m-phenylenediamine, N-isobutyl-p-phenylenediamine, N-isoamyl-p-phenylenediamine, N-cyclohexyl-p-phenylenediamine, N-benzyl-p-phenylenediamine, N-phenyl-p-phenylenediamine, N,N'-diethyl-p-phenylenediamine, N,N'-di(n-propyl)-p-phenylenediamine, N-methyl-N'-(n-propyl)-p-phenylenediamine, N-(n-butyl)-N'-benzyl-p-phenylenediamine, N,N'-dibenzyl-p-phenylenediamine, benzidine; N,N,N',N'-tetramethylbenzidine, 4,4'-oxydianiline, 4,4'-, 2,4'- and/or 2,2'-methylenedianiline, 4,4'-methylene-bis(N,N-dimethylaniline); 4,4'-methylene-bis(N-methylaniline), bis(3-methyl-4-aminophenyl)methane, 4,4'-ethylenedianiline, 2,4-diamino-N-phenylaniline, 2,4-bis(4-aminobenzyl)aniline, 1,2,4,5-tetraaminobenzene, bis(3,4-diaminophenyl)methane and combinations thereof.

In one embodiment of the process of the invention, the aromatic amine is 2,4-diaminotoluene and/or 2,6-diaminotoluene, and the reaction product comprises a mixture of 2,4-diamino-1-methyl-cyclohexane and 2,6-diamino-1-methyl-cyclohexane, wherein ≤50 mol % of said diamino-1-methyl-cyclohexane reaction products are in the cis-cis-isomer configuration and ≤15 mol % of said diamino-1-methyl-cyclohexanes reaction products are in the trans-trans-isomer configuration.

In another embodiment of the process of the invention, the metal of the heterogeneous catalyst is on a support selected from the group consisting of alumina, silica, titania, ceria, carbon and combinations thereof.

In another embodiment of the process of the invention, the metal of the first heterogeneous catalyst is ruthenium, rhodium, nickel or cobalt.

In another embodiment of the process of the invention, two heterogeneous catalysts are utilized, wherein the first heterogeneous catalyst is a supported ruthenium catalyst and the second heterogeneous catalyst is comprised of rhodium on silica, rhodium on alumina, nickel on silica, nickel on alumina, cobalt on silica or cobalt on alumina.

In another embodiment of the process of the invention, the organic nitro compound is selected from the group consisting of nitromethane, nitroethane, 1-nitropropane, 2-nitropropane, all isomers of nitrobutane, nitropentane and nitrohexane, 2-nitroheptane, 2-nitrooctane, nitrocyclopentane, nitrocyclohexane, 4-nitropyridine, 4-nitropiperidine, nitromethylbenzene, nitrobenzene, 4-fluoronitrobenzene, 4-chloronitrobenzene, 4-bromonitrobenzene, 2-nitroaniline, 3-nitroaniline, 4-nitroaniline, 2-nitrophenol, 3-nitrophenol, 4-nitrophenol, 1-methoxy-2-nitrobenzene, 1-methoxy-3-nitrobenzene, 1-methoxy-4-nitrobenzene, N-cyclohexylmethyl-4-nitroaniline, N-(1(4-nitrophenyl)ethyl)cyclohexaneamine, 2- and/or 4-nitrotoluene, 4-isopropylnitrobenzene, nitrostyrene, 4-nitrodiphenylmethane, 1-nitro-4-phenoxybenzene, 2,3-, 2,4-, 2,6- and 3,4-dinitrotoluene, and combinations thereof.

In another embodiment of the process of the invention, the aromatic amine is 2,4-diaminotoluene and/or 2,6-diaminotoluene and the reaction product comprises a mixture of 2,4-diamino-1-methyl-cyclohexane and 2,6-diamino-1-methyl-cyclohexane, wherein ≤50 mol % of said diamino-1-methyl-cyclohexane reaction products are in the cis-cis-isomer configuration and ≤15 mol % of said diamino-1-methyl-cyclohexanes reaction products are in the trans-trans-isomer configuration.

In another embodiment of the process of the invention, the metal of the heterogeneous catalyst is on a support selected from the group consisting of alumina, silica, titania, ceria, carbon and combinations thereof.

In another embodiment of the process of the invention, the metal of the first heterogeneous catalyst is ruthenium, rhodium, nickel or cobalt.

In another embodiment of the process of the invention, two heterogeneous catalysts are utilized, wherein the first heterogeneous catalyst is a supported ruthenium catalyst and the second heterogeneous catalyst is comprised of rhodium on silica, rhodium on alumina, nickel on silica, nickel on alumina, cobalt on silica or cobalt on alumina.

In another embodiment of the process of the invention, the organic nitro compound is selected from the group consisting of nitromethane, nitroethane, 1-nitropropane, 2-nitropropane, all isomers of nitrobutane, nitropentane and nitrohexane, 2-nitroheptane, 2-nitrooctane, nitrocyclopentane, nitrocyclohexane, 4-nitropyridine, 4-nitropiperidine, nitromethylbenzene, nitrobenzene, 4-fluoronitrobenzene, 4-chloronitrobenzene, 4-bromonitrobenzene, 2-nitroaniline, 3-nitroaniline, 4-nitroaniline, 2-nitrophenol, 3-nitrophenol, 4-nitrophenol, 1-methoxy-2-nitrobenzene, 1-methoxy-3-nitrobenzene, 1-methoxy-4-nitrobenzene, N-cyclohexylmethyl-4-nitroaniline, N-(1(4-nitrophenyl)ethyl)cyclohexaneamine, 2- and/or 4-nitrotoluene, 4-isopropylnitrobenzene, nitrostyrene, 4-nitrodiphenylmethane, 1-nitro-4-phenoxybenzene, 2,3-, 2,4-, 2,6- and 3,4-dinitrotoluene, and combinations thereof.

In another embodiment of the process of the invention, the process is conducted in the absence of at least one of Pd and Pt.

In another embodiment of the process of the invention, the organic nitro compound is added to the reactor during the course of the reaction.

In another embodiment of the process of the invention, the reactor is a trickle bed reactor.

In another embodiment of the process of the invention, the reaction is carried out at a temperature in the range from ≥120° C. to ≤250° C.

In another embodiment of the process of the invention, the molar ratio of catalytically active metal or metals in the heterogeneous catalyst or catalysts to organic nitro compound or organic nitro compounds is in a range of ≥0.01 to ≤10.

In another embodiment of the process of the invention, the catalytic system comprises a mixture of at least two heterogeneous catalysts, wherein the first and the second heterogeneous catalyst comprise a metal selected from the group consisting of Cr, Mo, W, Mn, Re, Fe, Ru, Os, Co, Rh, Ir, Ni, Pd, Pt and combinations thereof with the further proviso that the metal selected for the second heterogeneous catalyst is different from the metal selected for the first heterogeneous catalyst.

In another embodiment of the process of the invention, the first heterogeneous catalyst and the second heterogeneous catalyst are spatially separated from each other in the reactor.

DETAILED DESCRIPTION OF THE INVENTION

The process according to this invention provides a means for hydrogenating compounds having aromatic rings substituted with two or more primary amino groups with a higher rate to cycloaliphatic amines with two or more primary amino groups than those produced using state of the art catalysts or catalyst systems. The catalyst system according to the invention provides a high activity for hydrogenating less reactive aromatic amines with at least two amino groups bound to the same aromatic ring, compared to more reactive amines with at least two amino groups bound to different aromatic rings. The process according to this invention also provides a means for hydrogenating aromatic amines with two or more primary amino groups in meta or para position to each other to selectively obtain diastereomer mixtures with a sufficiently low percentage of cis-configuration. When the starting material is selected, e.g., from 2,6-diaminotoluene and/or 2,4-diaminotoluene, a sufficiently high percentage on a molar basis of the resulting diamino-1-methyl-cyclohexane compounds are in the cis-trans, trans-cis and trans-trans configuration.

The use of an organic nitro compound as additive in the reaction mixture facilitates catalyst preparation, as prior treatment of the catalyst with inorganic nitro compounds can be omitted. The use of an organic nitro compound also avoids the potential contamination of the product with salts resulting from leaching of the inorganic nitro compound.

Surprisingly, the inventors have found that the rate of the reaction is improved by the use of a catalyst system comprising a heterogeneous catalyst in combination with an organic nitro compound as additive, while a high chemoselectivity and a high diastereomer selectivity are maintained. The use of an organic nitro compound as an additive in the process according to the invention has the particular advantage that the additive can be chosen in such a way that hydrogenation of the organic nitro compound yields the same product as hydrogenation of the aromatic di- or polyamine, facilitating subsequent downstream processing.

The cycloaliphatic primary polyamines made according to this invention are useful for further reaction with polyepoxides or polyisocyanates. The primary amino groups of the hydrogenated products may also be converted to isocyanates via reaction with phosgene or through phosgene free methods. The resulting cycloaliphatic isocyanates with two or more isocyanate groups may be used as monomers for making polymers, such as polyurethanes or modified polyisocyanates useful as crosslinkers to form polyurethanes and/or polyureas. The cycloaliphatic primary polyamines may also be used for making active ingredients in the pharmaceutical industry.

The process according to this invention uses aromatic amines or a mixture of two or more aromatic amines as a starting material. The aromatic amine in the context of this invention is a compound having at least one aromatic ring and at least two amino groups bound to the aromatic system. The two amino groups may be bound to the same aromatic ring or may be bound to two different aromatic rings. In a preferred embodiment, at least two amino groups are bound to the same aromatic ring. When the aromatic amine has more than one aromatic ring, the rings may be condensed or joined by at least two common ring members, a bond between a ring member of each aromatic ring or a divalent moiety. The divalent moiety preferably comprises C, O, S or N, more preferably from 1 to 6 C atoms. In a preferred embodiment, the divalent moiety is methylene.

At least two substituents, preferably up to four substituents, and even more preferably two substituents of an aromatic amine, are amino groups. The amino groups are preferably primary or secondary amino groups, and more preferably primary amino groups. Preferably, at least one amino group is in the 2-, or 4-position, more preferably at least one amino group is in the 2-position relative to a hydrocarbon group, preferably a methyl group, on at least one, preferably only one, aromatic ring. More preferably, amino groups are present in the 2- and the 4- or 6-position of at least one, preferably only one, aromatic ring.

In general, examples of aromatic amines include aminobenzenes with two amino groups attached to the same aromatic ring system as represented in formula (VI),

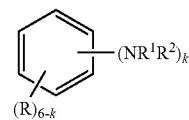

(VI)

wherein
R is hydrogen, halogen, linear or branched C1-C12 alkyl, linear or branched C1-C12 alkoxy, linear or branched C1-C12 alkoxyalkyl,
$R^1$ and $R^2$ are independently hydrogen, or linear or branched C1-C12 alkyl and
k is an integer from 2 to 4.

Other examples for aromatic amines include aminonaphthalenes with at least two amino groups attached to the aromatic ring system as represented in formula (VII),

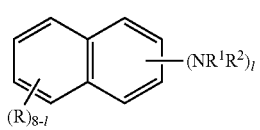

(VII)

wherein

R is hydrogen, halogen, linear or branched C1-C12 alkyl, linear or branched C1-C12 alkoxy, linear or branched C1-C12 alkoxyalkyl, $R_1$ and $R^2$ are independently hydrogen, or linear or branched C1-C12 alkyl, l is an integer from 2 to 4 and the substituents R and $NR^1R^2$ can be present at any position of the naphthalene ring.

Further examples include bridged polynuclear aromatic amines with two amino groups as represented in formula (VIII),

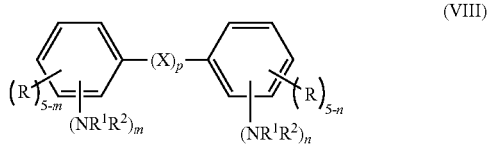

wherein
R is hydrogen, halogen, linear or branched C1-C12 alkyl, linear or branched C1-C12 alkoxy, linear or branched C1-C12 alkoxyalkyl, $R_1$ and $R^2$ are independently hydrogen, or linear or branched C1-C12 alkyl, X is linear or branched C1-C6 alkylene, O, S, $NR^3$ with $R^3$=linear or branched C1-C12 alkyl, m and n is 0 or an integer from 1 to 3 and m+n≥2 and
p is 0 or 1.

The process according to this invention uses a catalyst system comprising a heterogeneous catalyst and an organic nitro compound for conducting the hydrogenation of the aromatic amines.

The heterogeneous catalyst comprises a metal selected from the group consisting of Cr, Mo, W, Mn, Re, Fe, Ru, Os, Co, Rh, Ir, Ni, Pd and/or Pt. It is possible to employ a single catalyst, but a plurality of catalysts is also possible.

In the context of the present invention the term "heterogeneous catalyst" is meant to denote the combination of a catalytically active metal (Cr, Mo, W, Mn, Re, Fe, Ru, Os, Co, Rh, Ir, Ni, Pd and/or Pt) and a support.

The metal is preferably present on the support in the zero oxidation state, i.e., in elemental form. The corresponding oxide, hydroxide or other molecular compound may also be used, which is reduced to the metal prior to or during the hydrogenation of the aromatic amine. The metal is preferably present as nanoparticles, which have a volume-average particle size of ≥0.1 nm and ≤100 nm.

Preferably the metal comprises a single metal, whereby "single" includes technically unavoidable impurities. In an alternative embodiment, the metal comprises a main component of the above mentioned group and minor components of a second or more elements. The weight ratio of the main component to the minor component is preferably ≥80:≤20, more preferably ≥90: ≤10 and most preferably ≥95: ≤5.

The support is preferably a solid or gel material, which is preferably inert with respect to the aromatic amine and hydrogen under hydrogenation conditions. The support is preferably a particulate support. The particulate support may have a volume-average particle size of preferably ≥0.01 mm and ≤10 cm, more preferably ≥0.1 mm and ≤2 cm. Preferably, the support is a porous support.

The physical shape of the support may vary. The support particles may adopt the shape of a powder, pellets or extrudates. The surface area of the support is preferably ≥1 m²/g and ≤1000 m²/g, more preferably ≥10 m²/g and ≤800 m²/g and most preferably ≥50 m²/g and ≤600 m²/g. The surface area of the support can be determined using any method known to those of skill in the art. Suitable methods include the BET (Brunauer, Emmett & Teller) method using $N_2$ adsorption, such as described in DIN (Deutsches Institut fin Normung, e. V.) Standard 66131.

A wide range of support materials may be used. The support is preferably selected from the group comprising kappa, delta, gamma and theta alumina, silica, titania, zirconia, ceria, zeolites, such as ZSM-5, Beta, or mesoporous materials, such as SBA-15, polymer beads, such as beads of divinylbenzene-styrene-copolymer and/or carbon materials, such as active carbon or carbon nanotubes.

The metal may be bound chemically to the surface of the support, physisorbed on the surface of the support or encapsulated in pores of the support. The metal may also be encapsulated in the support and become accessible during the hydrogenation of the aromatic amines.

The weight ratio between the metal and the support is preferably ≥0.002 and ≤20, more preferably ≥0.005 and ≤5 and most preferably ≥0.01 and ≤0.1. Alternatively, the metal surface area is preferably ≥0.01 m²/g and ≤50 m²/g, more preferably ≥0.05 m²/g and ≤10 m²/g.

In an alternative embodiment at least two different heterogeneous catalysts are employed. The two heterogeneous catalysts may be present as a mixture or spatially separated in adjoined flow-through catalyst baskets or consecutive, alternating or nested catalyst beds.

The catalyst system further comprises an organic nitro compound. The organic nitro compound is an organic compound having at least one nitro substituent. Suitable organic nitro compounds are, e.g., $R^4NO_2$ wherein $R^4$ represents a linear or branched, optionally heteroatom-including C1- to C22-alkyl radical, a linear or branched, mono- or polysubstituted, optionally heteroatom-including C1- to C22-alkenyl radical, a mono- or polysubstituted, optionally heteroatom-including C6- to C18-aryl radical, member(s) of a saturated or unsaturated, optionally heteroatom-including 4- to 7-membered ring or polycyclic system.

The organic nitro compound is preferably a compound comprising one or more aromatic rings and/or one or more cycloaliphatic rings, wherein each ring may be unsubstituted or substituted with one or more methyl groups or substituted or unsubstituted aliphatic groups. When the organic compound comprises two or more rings, the rings may be fused or joined by at least one common ring member, a bond between a ring member of each ring or a divalent moiety. The divalent moiety preferably comprises linear or branched C1-C6 alkylene, O, S, $NR^3$ with $R^3$=linear or branched C1-C12 alkyl, more preferably C1-C6 alkylene. In a preferred embodiment, the divalent moiety is methylene.

When the organic nitro compound comprises one or more rings, each ring preferably has 5 to 7, more preferably 6, ring members, wherein the ring members preferably comprise C, N, or Si, more preferably at least 3, more preferably at least 4, and even more preferably at least 5, ring members are carbon atoms, even more preferably all ring members are carbon atoms. Each ring is preferably a benzene ring.

Each ring member of the organic compound having one or more rings may be unsubstituted or substituted. Preferred substituents include hydrocarbon groups having from 1 to 12 carbon atoms and, optionally, 1 to 3 heteroatoms preferably selected from N, O and S, and groups having at least one hetero atom bound directly to a ring member, wherein the hetero atoms are preferably selected from N, O and S, which may further have one or more H or a branched or linear, saturated or unsaturated hydrocarbon group substituents having from 1 to 12 carbon atoms. The aforementioned hydrocarbon carbons are each preferably selected from methyl, ethyl, n-propyl, isopropyl, n-butyl, isobutyl, or tert-butyl, and more preferably methyl. The ring preferably has from zero to three, more preferably zero or one hydrocarbon group substituent, which is preferably a methyl group.

Each nitro group is preferably a ring substituent of the organic compound having one or more rings. In a preferred embodiment, at least two ring substituents, preferably up to four ring substituents, and even more preferably only two ring substituents, are nitro groups. Each nitro group is preferably bound directly to a ring member of an organic compound having at least one ring member, wherein the ring is preferably an aromatic ring, more preferably a benzene ring.

The organic nitro compound may also be described by the formulas presented in connection with aromatic amines, where the $NR^1R^2$ substituents are $NO_2$ groups.

The organic nitro compound is preferably soluble in an organic solvent. In a preferred embodiment, the organic nitro compound is soluble in a solvent having one or more ether or alcohol groups. In a particularly preferred aspect of this invention, the solvent is diethylether, dipropylether, dibutylether, methyl-butylether, tetrahydrofuran, 1,3-dioxane, 1,4-dioxane, or tetrahydro-2H-pyran. In another embodiment of this invention, the solvent is n-propanol, iso-propanol, n-butanol, iso-butanol, or tert-butanol.

The catalytic system may contain one organic nitro compound or a combination of two or more organic nitro compounds. The weight ratio of the organic nitro compound to the other components of the catalyst system is preferably in a range of ≥0.0001 to ≤100, more preferably ≥0.001 to ≤50 and most preferably ≥0.01 to ≤10. In the case of a batch reactor, the calculation of this weight ratio is straightforward. In flow-type reactors where, for example, the aromatic amine(s) and the organic nitro compound may pass through a catalyst bed together, the known concentration of the organic nitro compound in the aromatic amine(s), the volume of the reactor section with the catalyst bed and the volume of the catalyst itself may be used to calculate the amount of organic nitro compound present in the catalyst bed section of the reactor and hence its weight ratio may be deduced.

It should be noted that the organic nitro compound is to be understood as actually being from an external source in the course or in preparation of the method according to the invention. Specifically, impurities in the aromatic amine as source for the organic nitro compound are excluded. Likewise, it is possible that the compound derived from the organic nitro compound in which the nitro groups are exchanged by amino groups differs from the aromatic amine used as starting material in the method according to the invention.

The reaction is preferably conducted under a pressure greater than atmospheric pressure. In one embodiment, the pressure is at least 20 bar (20 kPa), more preferably at least 50 bar (50 kPa), and even more preferably at least 80 bar (80 kPa).

Suitable reactors for the hydrogenation of the aromatic amine include a stirred tank reactor, tubular reactor and a loop reactor. A particularly suitable reactor is a stirred tank reactor with gas entrainment, whereby the heat of reaction is preferably removed with an internal or external heat exchanger.

Another particularly suitable reactor is a trickle bed reactor, whereby the flow direction of the hydrogen and the liquid phase are in the same direction upwards or downwards with respect to gravity (up-flow or down-flow), or in the opposite direction (counter-flow).

The hydrogenation of the aromatic amine can be performed in batch, semi-batch or continuous operation. In a preferred embodiment, the hydrogenation of the aromatic amine is performed in semi-batch operation, whereby the consumed hydrogen is replaced by feeding hydrogenation. In another preferred embodiment of the invention, the hydrogenation of the aromatic amine is performed in a continuous operation, whereby the aromatic amine and hydrogen are continuously fed to the reactor and the product mixture is continuously removed from the reactor.

The components of the catalyst system can be added to the reaction mixture separately or as a mixture at the same time. In batch and semi-batch processes, the components of the catalyst system can be added to the reaction mixture at different times. In an alternative embodiment of the invention, a first heterogeneous catalyst and a second heterogeneous catalyst are added at different times to the reaction mixture or are placed spatially separated in adjoined flow-through catalyst baskets. The organic nitro compound may be charged into the reactor before, together with or subsequent to the catalyst. In a preferred embodiment of the invention, the organic nitro compound is added simultaneously with the amine, preferentially as a mixture or solution with the amine.

In continuous processes, the aromatic amine and hydrogen are continuously fed to the reactor and the product mixture is continuously removed from the reactor. In an alternative embodiment of the invention, a first heterogeneous catalyst and a second heterogeneous catalyst may be placed into the reactor as a mixture or separately in consecutive, alternating or nested beds. The organic nitro compound may be part of the heterogeneous catalyst placed into the reactor or added simultaneously with the amine, preferentially as a mixture with the amine. The amount of aromatic amine (in kg) intended for hydrogenation can be from ≥0.01 to ≤20, and more typically from ≥0.1 to ≤5 per 1 liter of catalyst per hour.

The reaction may be carried out in the presence of an inert solvent. The solvent is preferentially an organic solvent.

Further aspects and embodiments of the present invention will be described below. They may be combined freely unless the context clearly indicates otherwise.

In one embodiment of the process according to the invention the aromatic amine is selected from the group consisting of o-, m-, and p-phenylenediamine, 2,3-diaminotoluene, 2,4-diaminotoluene, 2,6-diaminotoluene, 3,4-diaminotoluene, 2,3-diamino-p-xylene, 2,5-diamino-p-xylene, 2,6-diamino-p-xylene, N-methyl-o-phenylenediamine, N-ethyl-o-phenylenediamine, 4-methoxy-m-phenylenediamine, N-methyl-m-phenylenediamine, N-ethyl-m-phenylenediamine, N-isobutyl-p-phenylenediamine, N-isoamyl-p-phenylenediamine, N-cyclohexyl-p-phenylenediamine, N-benzyl-p-phenylenediamine, N-phenyl-p-phenylenediamine, N,N'-diethyl-p-phenylenediamine, N,N'-di(n-propyl)-p-phenylenediamine, N-methyl-N'-(n-propyl)-p-phenylenediamine, N-(n-butyl)-N'-benzyl-p-phenylenediamine, N,N'-dibenzyl-p-phenylenediamine, benzidine; N,N,N',N'-tetramethylbenzidine, 4,4'-oxydianiline, 4,4'-, 2,4'- and/or 2,2'-methylenedianiline, 4,4'-methylene-bis(N,N-dimethylaniline); 4,4'-methylene-bis(N-methylaniline), bis(3-medthyl-4-aminophenyl)methane, 4,4'-ethylenedianiline, 2,4-diamino-N-phenylaniline, 2,4-bis(4-aminobenzyl)aniline, 1,2,4,5-tetraaminobenzene, and/or bis(3,4-diaminophenyl)methane.

In another embodiment of the process according to the invention, the aromatic amine is 2,4-diaminotoluene and/or 2,6-diaminotoluene. If mixtures are used the weight percentage of the 2,6-diaminotoluene in the sum of 2,4-diaminotoluene and 2,6-diaminotoluene is preferably in the range up to 98%, more preferably in the range up to 80% and most preferably in the range up to 40%.

In another embodiment of the process according to the invention 2,4-diaminotoluene and/or 2,6-diaminotoluene are used as aromatic amines and the reaction product comprises a mixture of 2,4-diamino-1-methyl-cyclohexane and 2,6-diamino-1-methyl-cyclohexane wherein ≤50 mol % of the diamino-1-methyl-cyclohexanes are in the cis-cis-isomer configuration and ≤15 mol % of the diamino-1-methyl-cyclohexanes are in the trans-trans-isomer configuration.

In another embodiment of the process according to the invention the metal of the heterogeneous catalyst is on a support selected from the group consisting of alumina, silica, titania, ceria and/or carbon.

In another embodiment of the process according to the invention the metal of the heterogeneous catalyst is ruthenium, rhodium, nickel or cobalt.

In another embodiment of the process according to the invention two heterogeneous catalysts are used whereby the first heterogeneous catalyst is a supported ruthenium catalyst and the second heterogeneous catalyst is rhodium on silica, rhodium on alumina, nickel on silica, nickel on alumina, cobalt on silica or cobalt on alumina.

In another embodiment of the process according to the invention the organic nitro compound is selected from the group of nitromethane, nitroethane, 1-nitropropane, 2-nitropropane, all isomers of nitrobutane, nitropentane and nitrohexane, 2-nitroheptane, 2-nitrooctane, nitrocyclopentane, nitrocyclohexane, 4-nitropyridine, 4-nitropiperidine, nitromethylbenzene, nitrobenzene, 4-fluoronitrobenzene, 4-chloronitrobenzene, 4-bromonitrobenzene, 2-nitroaniline, 3-nitroaniline, 4-nitroaniline, 2-nitrophenol, 3-nitrophenol, 4-nitrophenol, 1-methoxy-2-nitrobenzene, 1-methoxy-3-nitrobenzene, 1-methoxy-4-nitrobenzene, N-cyclohexylmethyl-4-nitroaniline, N-(1(4-nitrophenyl)ethyl)cyclohexaneamine, 2- and/or 4-nitrotoluene, 4-isopropylnitrobenzene, nitrostyrene, 4-nitrodiphenylmethane, 1-nitro-4-phenoxybenzene and/or 2,3-, 2,4-, 2,6- and/or 3,4-dinitrotoluene. Preferred organic nitro compounds are nitromethane, nitroethane, nitrobenzene, nitroaniline and the isomers of dinitrotoluene.

In another embodiment of the process according to the invention the process is conducted in the absence of Pd and/or Pt.

In another embodiment of the process according to the invention the organic nitro compound is added to the reactor during the course of the reaction.

In another embodiment of the process according to the invention the reactor is a trickle bed reactor. Particularly preferred is the combination of a trickle bed reactor with spatially separated first and second catalysts as will be described in more detail below. Zones with the first catalyst may be adjacent to zones with the second catalyst (as seen in the flow direction of the reaction mixture), or there may be inert sections between the catalyst zones.

In another embodiment of the process according to the invention the reaction is carried out at a temperature in the range from ≥120° C. to ≤250° C. Preferred reaction temperatures are ≥130° C. to ≤200° C., more preferred ≥140° C. to ≤180° C.

In another embodiment of the process according to the invention the reaction is carried out in the presence of a solvent having ether or alcohol groups. Examples for such solvents include diethylether, dipropylether, dibutylether, methyl-butylether, tetrahydrofuran, 1,3-dioxane, 1,4-dioxane, or tetrahydro-2H-pyran, n-propanol, iso-propanol, n-butanol, iso-butanol and/or tert-butanol.

In another embodiment of the process according to the invention the molar ratio of catalytically active metal or metals in the heterogeneous catalyst or catalysts to organic nitro compound or organic nitro compounds is in a range of ≥0.01 to ≤10. Preferably this molar ratio is ≥0.05 to ≤8, more preferably ≥0.4 to ≤5.

In another embodiment of the process according to the invention the catalytic system comprises a mixture of at least two heterogeneous catalysts, wherein the first and the second heterogeneous catalyst comprise a metal selected from the group consisting of Cr, Mo, W, Mn, Re, Fe, Ru, Os, Co, Rh, Ir, Ni, Pd and/or Pt with the further proviso that the metal selected for the second heterogeneous catalyst is different from the metal selected for the first heterogeneous catalyst.

A "mixture" of the two catalysts may be simply a physical mixture of a first metal on a first support and a second metal on a second support. In any case, the catalyst system according to the invention is not to be understood as being the result of a co-precipitation of two metals onto a shared support as this would not meet the criterion of having two distinct catalysts. Likewise, the case of a first metal on a support doped with a second metal is also excluded.

Here the catalyst system comprises at least two metals selected from the aforementioned group. Each metal is preferably independently combined with a support to form a heterogeneous catalyst prior to combining the heterogeneous catalyst with a heterogeneous catalyst comprising a different metal. When the support of a heterogeneous catalyst is a particulate support, each particle of the particulate support is preferably combined with only one metal selected from the group of metals listed above.

The catalyst system may comprise a first heterogeneous catalyst comprising a first metal selected from the above group combined with a first support and a second heterogeneous catalyst comprising a second metal selected from the above group, which is different from the first metal combined with a second support, wherein the chemical composition of the first support and the second support may be the same or different. The weight part of the second heterogeneous catalyst with respect to the entire catalyst system is preferred to be ≥0.1 weight-%, more preferred ≥1 weight-% and most preferred ≥5 weight-%.

It is possible that the metal of the first heterogeneous catalyst and the metal of the second heterogeneous catalyst are present as individual nanoparticles on a common support. The nanoparticles of the metals have a volume-average particle size of preferably ≥0.1 nm and ≤100 nm. The two types of nanoparticles may be mixed and combined with the support to form the catalyst system.

The catalyst system may further comprise a third heterogeneous catalyst comprising the first or second metal selected from the above group, which is combined with a third support, wherein the chemical composition of the third support is different from that of the first and the second support.

The catalyst system may also comprise additional heterogeneous catalysts analogous to the first, second and third heterogeneous catalyst.

In the foregoing embodiments, each support is preferably a particulate support. More preferably, each and every support is a particulate support.

The catalyst system may further comprise a third heterogeneous catalyst comprising a third metal selected from the above group, which is different from the first metal and the second metal combined with a third support, wherein the chemical composition of the third support may be the same or different from that of the first particulate support and the second support.

It is also preferred that the first heterogeneous catalyst and the second heterogeneous catalyst are spatially separated from each other in the reactor. Using separate reaction zones may further improve the selectivity in certain reactions. An example would be to first hydrogenate in the presence of the first catalyst in a first reaction zone or reaction vessel and then transfer the product mixture to a second reaction zone or reaction vessel. Preferably a Ru-containing catalyst is the first catalyst. Placing the two heterogeneous catalysts separated from each other into the reaction can also facilitate recycling of the metal in the catalysts after their use.

A further aspect of the present invention is the use of a catalytic system for hydrogenating aromatic di- and polyamines, wherein the catalytic system comprises a heterogeneous catalyst, wherein the heterogeneous catalyst comprises a metal selected from the group consisting of Cr, Mo, W, Mn, Re, Fe, Ru, Os, Co, Rh, Ir, Ni, Pd and/or Pt and wherein the catalyst system further comprises an organic nitro compound.

All other aspects and embodiments of the catalyst system discussed above with respect to the process according to the invention may be applied to the use according to the invention. For reasons of brevity they are not repeated here.

The invention is further illustrated by way of the following examples, which are not intended to limit the overall scope of this invention.

EXAMPLES

The abbreviations used in the following examples are defined below:

| Designation | Definition |
|---|---|
| Ru1 | 5 wt. % Ru on $Al_2O_3$ from BASF (product no. 57497196) |
| Ru2 | 5 wt. % Ru on $Al_2O_3$ from Johnson Matthey Co. (product no. M11185) |
| Rh1 | 5 wt. % Rh on $Al_2O_3$ from Johnson Matthey Co. (product no. M11196) |
| Ni1 | 46.6 wt. % Ni on $SiO_2$ from Johnson Matthey Co. (product no. 0812/2011) |
| 2,4-TDA | 2,4-Toluenediamine (98%) |
| 2,6-TDA | 2,6-Toluenediamine (97%) |
| NB | Nitrobenzene (≥99%) |
| DNT | 2,4-Dinitrotoluene (97%) |
| $MeNO_2$ | Nitromethane (≥96%) |

Test Protocol

If not stated otherwise, the starting material, namely a mixture of 0.64 g 2,4-TDA and 0.16 g 2,6-TDA in 90 ml tetrahydrofuran (THF), together with the catalyst system specified in the tables below, were charged into a pressurizable stainless steel autoclave vessel having a volume of 160 ml. The mixture was stirred using a gas entrainment stirrer at a rate of 600 revolutions per minute and heated to the temperature, T. When the catalysts Ru1, Ni1 or mixtures of both catalysts were used, the temperature T was set to 160° C. When the catalysts Ru2, Rh1 or mixtures of both catalysts were used, the temperature T was set to 140° C. The autoclave vessel was then pressurised with hydrogen to 100 bar (100 kPa). The mixture was stirred continuously for a total of 450 minutes, while holding the temperature constant at the specified temperature and the pressure in the autoclave vessel constant at 100 bar (100 kPa) by feeding further hydrogen from a hydrogen holding tank having a known volume and pressure into the mixture to compensate for hydrogen used by the reaction. At the end of the 450 minute time period allotted for the reaction, the feeding of hydrogen gas was discontinued, the autoclave vessel cooled to 25° C. and the pressure within the autoclave vessel carefully released down to atmospheric pressure. The liquid product mixture was removed from the vessel, filtered and subjected to gas chromatography to determine the composition of the product mixture.

The rate of hydrogen consumption per minute was calculated from the drop in pressure in the hydrogen holding tank. The pressure drop was recalculated to the amount of hydrogen consumed. The data for the amount of hydrogen consumed as a function of time were fitted with equation (IX):

$$n_{H2}(t) = a\left(1 - \frac{1}{1+b \times t}\right) + (c \times t), \quad (IX)$$

where $n_{H2}(t)$ is the amount of hydrogen consumed with time, t is the time and a, b and c are real numbers used as fit parameters, which were varied until the least squares difference between the measured and the fitted data was minimal.

The initial reaction rate at time zero was calculated according to equation (X) by extrapolation of data collected for the rate of hydrogen consumption backward in time to time equals zero:

$$\text{Initial rate} = \frac{ab+c}{m(\text{cat})}, \quad (X)$$

where a, b and c have the above mentioned meaning and m(cat) is the mass of the heterogeneous catalyst employed.

The relative amounts of remaining 2,4-TDA and 2,6-TDA, the formed primary amines thereby distinguishing the ortho and para ring-position isomers and the relative amounts of cis and trans isomers as well as deaminated monoamines and small amounts of binuclear secondary amines were determined by gas chromatography using a Hewlett Packard Model HP 6890 gas chromatography apparatus. The column used in gas chromatography was CP-Sil-PONA-CB (silica) with a length of 50 m and inner diameter of 0.21 mm. The carrier gas was helium with a constant flow of 1.5 ml/min. The injector temperature was set at 250° C. and the detector temperature was set at 300° C. For each sample, the gas chromatography temperature program was set to hold the column at a temperature of 110° C. for 20 minutes, after which the temperature of the column was ramped to a temperature of 250° C. at a rate of 10° C. per minute and then maintained at 250° C. for 10 minutes. The resulting areas under the peaks of the chromatograms were converted into mass fractions in wt % and the conversions were calculated according to equation (XI)

$$\text{Conversion} = \left(1 - \frac{c_{TDA}(t)}{\sum c_i}\right), \quad (XI)$$

where $c_{TDA}(t)$ is the concentration of TDA at the end of the experiment and $\Sigma\, c_i$ is the sum of the concentrations of TDA and all detected products.

The chemoselectivity to ring hydrogenated diamines was calculated according to equation (XII)

$$\text{Chemoselectivity} = \left(\frac{C_{Diamino-methyl-cyclohexane}}{\Sigma\, c_j}\right) \times 100\%, \qquad \text{(XII)}$$

where $C_{Diamino-methyl-cyclohexane}$ is the sum of the concentration of all 2,4-diamino-1-methyl-cyclohexane and 2,6-diamino-1-methyl-cyclohexane isomers and $\Sigma\, c_j$ is the sum of the concentrations of all detected products.

The isomer content was calculated according to equation (XIII)

$$\text{Isomer content} = \frac{C_{Isomer}}{C_{Diamino-methyl-cyclohexane}}, \qquad \text{(XIII)}$$

Where $C_{Isomer}$ is the diamino-methyl-cyclohexane isomer for which the isomer content is calculated.

The hydrogenation products of 2,4-TDA and 2,6-TDA are compositions comprising a mixture of diastereomers. The designations cis and trans refer to the positions of the respective amino groups relative to the position of the methyl group in the hydrogenated product. When 2,4-diamino-1-methyl-cyclohexane is made from 2,4-TDA, the first designation cis or trans refers to the position of the amino group in the ortho-position and the second designation cis or trans refers to the position of the amino group in the para-position, each relative to the methyl group. When 2,6-diamino-1-methyl-cyclohexane is made from 2,6-TDA, cis and trans refers to the position of the two amino groups in the ortho-position relative to the methyl group.

The following table summarizes the diastereomer permutations available for the 2,4-diamino and 2,6-diamino ring-position isomers and their retention times measured by gas chromatography as described above.

| Product | ortho-Position | para-Position | Retention Time |
|---|---|---|---|
| 2,4-Diamino-1-methyl-cyclohexane | trans | cis | 14.14 minutes |
|  | cis | trans | 14.51 minutes |
|  | trans | trans | 13.56 minutes |
|  | cis | cis | 15.58 minutes |
| 2,6-Diamino-1-methyl-cyclohexane | trans-trans | — | 13.95 minutes |
|  | cis-trans | — | 14.81 minutes |
|  | cis-cis | — | 16.31 minutes |

In the following examples, the hydrogenation of aromatic di- and polyamines was conducted in accordance with the above test protocol using the catalyst systems and reaction temperatures specified below. The results obtained are reported in the following tables.

Example 1

Hydrogenation of a Mixture of 2,4-TDA and 2,6-TDA Using Ruthenium Catalyst Ru1 in the Presence of an Organic Nitro Compound Table 1A below shows data obtained for Examples 1a to 1h according to this invention and Comparative Examples 1i* and 1j* by conducting the hydrogenation using Ru1 (0.25 g) as the heterogeneous catalyst according to the above test protocol. The hydrogenation in Comparative Example 1i* was conducted in the same way as in Examples 1a to 1h, except that an organic nitro compound was absent. The hydrogenation in Comparative Example 1j* was conducted in the same way as in Examples 1a to 1h, except that NaNO$_2$ was used as an inorganic nitro compound.

TABLE 1A

COMPARISON OF INITIAL REACTION RATES, CONVERSIONS AND CHEMOSELECTIVITIES FOR CATALYST SYSTEMS ACCORDING TO THE INVENTION RELATIVE TO COMPARATIVE CATALYST SYSTEMS

| Example | DNT grams | NB grams | MeNO$_2$ grams | NaNO$_2$ grams | Initial Rate mol$_{H_2}$/min/g$_{cat}$ | Conversion percent | Selectivity percent |
|---|---|---|---|---|---|---|---|
| 1a | 0.010 | 0 | 0 | 0 | 0.0027 | 100 | 91.1 |
| 1b | 0.020 | 0 | 0 | 0 | 0.0041 | 98.5 | 90.6 |
| 1c | 0.040 | 0 | 0 | 0 | 0.0030 | 97.2 | 90.6 |
| 1d | 0 | 0.005 | 0 | 0 | 0.0021 | 99.9 | 90.6 |
| 1e | 0 | 0.010 | 0 | 0 | 0.0024 | 100 | 89.6 |
| 1f | 0 | 0.020 | 0 | 0 | 0.0046 | 100 | 89.1 |
| 1g | 0 | 0 | 0.001 | 0 | 0.0024 | 99.5 | 91.3 |
| 1h | 0 | 0 | 0.005 | 0 | 0.0021 | 99.9 | 90.7 |
| 1i* | 0 | 0 | 0 | 0 | 0.0016 | 99.6 | 89.6 |
| 1j* | 0 | 0 | 0 | 0.010 | 0.0003 | 99.6 | 93.2 |

The data in Table 1A show that the addition of DNT, NB and MeNO$_2$, according to this invention, results in an increase in the initial reaction rate relative to Comparative Example 1a*, in which DNT, NB and MeNO$_2$ were absent, and Comparative Example 1j*, in which NaNO$_2$ was used as inorganic nitro compound. The desired high conversion and chemoselectivity is maintained in the presence of an organic nitro-additive relative to Comparative Example 1j*. In Examples 1a to 1c the use of 2,4-dinitrotoluene as organic nitro compound according to the invention provided an additional amount of 2,4-diamino-1-methyl-cyclohexane. The less complex product mixture which does not contain sodium salts facilitates subsequent downstream processing.

Table 1B shows the effect of DNT, NB and MeNO$_2$ on diastereomer selectivity for Examples 1a to 1h according to this invention relative to Comparative Example 1i*, in which DNT, NB or MeNO$_2$ were absent and Comparative Example 1j*, in which NaNO$_2$ was used as an inorganic nitro compound.

TABLE 1B

COMPARISON OF CIS AND TRANS ISOMER CONTENT OF REACTION PRODUCTS MADE USING CATALYST SYSTEMS ACCORDING TO THE INVENTION RELATIVE TO COMPARATIVE CATALYST SYSTEMS

| Reaction Product | ortho-Position | para-Position | Ex. 1a % | Ex. 1b % | Ex. 1c % | Ex. 1d % | Ex. 1e % | Ex. 1f % | Ex. 1g % | Ex. 1h % | Comp. Ex. 1i* % | Comp. Ex. 1j* % |
|---|---|---|---|---|---|---|---|---|---|---|---|---|
| 2,4-Diamino-1-methyl-cyclohexane | trans | cis | 12 | 12 | 12 | 13 | 13 | 12 | 12 | 12 | 10 | 23 |
|  | cis | trans | 27 | 25 | 25 | 27 | 27 | 26 | 25 | 26 | 20 | 13 |
|  | trans | trans | 11 | 9 | 10 | 11 | 11 | 12 | 11 | 11 | 7 | 27 |

TABLE 1B-continued

COMPARISON OF CIS AND TRANS ISOMER CONTENT OF REACTION PRODUCTS MADE USING CATALYST SYSTEMS ACCORDING TO THE INVENTION RELATIVE TO COMPARATIVE CATALYST SYSTEMS

| Reaction Product | ortho-Position | para-Position | Ex. 1a % | Ex. 1b % | Ex. 1c % | Ex. 1d % | Ex. 1e % | Ex. 1f % | Ex. 1g % | Ex. 1h % | Comp. Ex. 1i* % | Comp. Ex. 1j* % |
|---|---|---|---|---|---|---|---|---|---|---|---|---|
| 2,6-Diamino-1-methyl-cyclohexane | cis | cis | 34 | 38 | 37 | 33 | 32 | 33 | 35 | 33 | 46 | 20 |
| | trans-trans | — | 2 | 1 | 1 | 2 | 2 | 2 | 2 | 2 | 1 | 3 |
| | cis-trans | — | 7 | 7 | 7 | 7 | 7 | 7 | 7 | 7 | 6 | 9 |
| | cis-cis | — | 7 | 8 | 8 | 7 | 8 | 8 | 8 | 8 | 10 | 5 |

As can be seen from the data presented in Table 1B, the desired high proportion of the trans-cis, cis-trans and trans-trans 2,4-diamino-1-methyl-cyclohexane isomers is maintained in the presence of an organic nitro-additive relative to Comparative Examples 1i* and 1j*. Likewise, the desired high proportion of the trans-trans and cis-trans 2,6-diamino-1-methyl-cyclohexane isomers is maintained in the presence of an organic nitro-additive relative to Comparative Examples 1i* and 1j*.

Example 2

Hydrogenation of a Mixture of 2,4-TDA and 2,6-TDA Using Rhodium Catalyst Rh1 and in the Presence of an Organic Nitro Compound Table 2 below shows data obtained for Example 2 according to this invention and Comparative Example 2* by conducting the hydrogenation using Rh1 (0.27 g) as the sole heterogeneous catalyst according to the above test protocol. Hydrogenation Example 2 was conducted with a catalyst system comprising, in addition to the heterogeneous catalyst, DNT. The hydrogenation in Comparative Example 2* was conducted in the same way as in Example 2, except that the hydrogenation was conducted in the presence of $NaNO_2$ instead of DNT.

TABLE 2

COMPARISON OF INITIAL REACTION RATES, CONVERSIONS AND CHEMOSELECTIVITIES FOR CATALYST SYSTEMS ACCORDING TO THE INVENTION RELATIVE TO A COMPARATIVE CATALYST SYSTEM

| Example | DNT grams | $NaNO_2$ grams | Initial Rate $molH_2/min/g_{cat}$ | Conversion percent | Selectivity percent |
|---|---|---|---|---|---|
| 2 | 0.01 | 0 | 0.0155 | 100 | 81.3 |
| 2* | 0 | 0.01 | 0.0078 | 98.3 | 78.9 |

The data in Table 2 show that the addition of DNT, according to this invention, results in an increase in the initial reaction rate relative to Comparative Example 2*, in which $NaNO_2$ was used. The addition of DNT, according to this invention, also results in a higher conversion and improved chemoselectivity relative to Comparative Example 2*, in which $NaNO_2$ was used. In example 2 the use of 2,4-dinitrotoluene as organic nitro compound according to the invention provided an additional amount of 2,4-diamino-1-methyl-cyclohexane. The less complex product mixture which does not contain sodium salts facilitates subsequent downstream processing.

The diastereomer ratios of the product obtained in Example 2 were substantially the same as those of the product obtained according to Comparative Example 2*.

Example 3

Hydrogenation of a Mixture of 2,4-TDA and 2,6-TDA Using a Mixture of Ruthenium Catalyst Ru1 and Nickel Catal St Ni1 in the Presence of an Organic Nitro Compound Table 3A below shows data obtained for Examples 3a to 3b according to this invention and Comparative Example 3* by conducting the hydrogenation using a combination of Ru1 (0.24 g) and Ni1 (0.002 g) as the heterogeneous catalyst according to the above test protocol. Hydrogenation Examples 3a to 3b were conducted with a catalyst system comprising, in addition to the heterogeneous catalyst, an organic nitro compound. The hydrogenation in Comparative Example 3* was conducted in the same way as in Example 3a, except that DNT was absent.

TABLE 3A

COMPARISON OF INITIAL REACTION RATES, CONVERSIONS AND CHEMOSELECTIVITIES FOR CATALYST SYSTEMS ACCORDING TO THE INVENTION RELATIVE TO A COMPARATIVE CATALYST SYSTEM

| Example | DNT grams | NB grams | Initial Rate $molH_2/min/g_{cat}$ | Conversion percent | Selectivity percent |
|---|---|---|---|---|---|
| 3a | 0.01 | 0 | 0.0036 | 99.6 | 90.9 |
| 3b | 0 | 0.01 | 0.0030 | 99.7 | 90.3 |
| 3* | 0 | 0 | 0.0004 | 100.0 | 89.0 |

The data in Table 3A show that the addition of DNT and NB, according to this invention, results in an increase in the initial reaction rate as well as an improved chemoselectivity relative to Comparative Example 3*, in which DNT and NB were absent. The desired high conversion is maintained in the presence of an organic nitro-additive relative to Comparative Example 3*.

Table 3B shows the effect of DNT and NB on diastereomer selectivity for Examples 3a to 3b according to this invention relative to Comparative Example 3*, in which DNT or NB were absent.

TABLE 3B

COMPARISON OF CIS AND TRANS ISOMER CONTENT OF REACTION PRODUCTS MADE USING CATALYST SYSTEMS ACCORDING TO THE INVENTION RELATIVE TO A COMPARATIVE CATALYST SYSTEM

| Reaction Product | ortho-Position | para-Position | Ex. 3a % | Ex. 3b % | Comp. Ex. 3* % |
|---|---|---|---|---|---|
| 2,4-Diamino-1-methyl-cyclohexane | trans | cis | 12 | 11 | 18 |
| | cis | trans | 28 | 29 | 13 |
| | trans | trans | 10 | 11 | 29 |

TABLE 3B-continued

COMPARISON OF CIS AND TRANS ISOMER CONTENT
OF REACTION PRODUCTS MADE USING CATALYST
SYSTEMS ACCORDING TO THE INVENTION RELATIVE
TO A COMPARATIVE CATALYST SYSTEM

| Reaction<br>Product | ortho-<br>Position | para-<br>Position | Ex. 3a % | Ex. 3b % | Comp.<br>Ex. 3* % |
|---|---|---|---|---|---|
|  | cis | cis | 33 | 33 | 24 |
| 2,6-Diamino-1- | trans-trans | — | 2 | 2 | 2 |
| methyl- | cis-trans | — | 8 | 8 | 8 |
| cyclohexane | cis-cis | — | 7 | 6 | 6 |

As can be seen from the data presented in Table 3B, the desired high proportion of the trans-cis, cis-trans and trans-trans 2,4-diamino-1-methyl-cyclohexane isomers is maintained in the presence of an organic nitro-additive relative to Comparative Example 3*. Likewise, the desired high proportion of the trans-trans and cis-trans 2,6-diamino-1-methyl-cyclohexane isomers is maintained in the presence of an organic nitro-additive relative to Comparative Example 3*.

Example 4

Hydrogenation of a Mixture of 2,4-TDA and
2,6-TDA Varying the Amount of Substrate Using
Different Catalysts in the Presence of an Organic
Nitro Compound Table 4 below shows data obtained for Examples 4a to 4d according to this invention by conducting the hydrogenation using different catalysts as the heterogeneous catalysts according to the above test protocol, but increasing the amount of TDA (mixture of regioisomers in a ratio of 80% of 2,4-TDA and 20% of 2,6-TDA) relative to the amount of THF. Hydrogenation Examples 4a to 4d were conducted at the temperature (T) stated in the table with catalyst systems comprising, in addition to the heterogeneous catalysts, DNT.

TABLE 4

COMPARISON OF INITIAL REACTION RATES, CONVERSIONS
AND CHEMOSELECTIVITIES FOR CATALYST SYSTEMS
ACCORDING TO THE INVENTION AT A HIGHER
SUBSTRATE CONCENTRATION

| Example | TDA grams | $V_{THF}$ mL | Catalyst System | Initial Rate $mol_{H_2}/min/g_{cat}$ | Conversion percent | Selectivity percent |
|---|---|---|---|---|---|---|
| 4a | 10 | 80 | 2.40 g Ru1<br>0.10 g DNT | 0.0013 | 97.4 | 86.8 |
| 4b | 10 | 80 | 3.00 g Ru1<br>0.02 g Ni1<br>0.10 g DNT | 0.0009 | 100 | 86.8 |
| 4c | 30 | 60 | 9.00 g Ru1<br>0.06 g Ni1<br>0.30 g DNT | 0.0011 | 99.6 | 81.9 |
| 4d | 20 | 80 | 2.90 g Ru2<br>0.34 g Rh1<br>0.10 g DNT | 0.0027 | 99.6 | 86.2 |

The data in Table 4 show that also at high concentrations of TDA high initial reaction rates are obtained with catalyst systems according to this invention. The desired high conversions and chemoselectivities are maintained.

Example 5

Hydrogenation of a Mixture of 2,4-TDA and
2,6-TDA Using Different Catalyst in the Presence of
a Large Amount of an Organic Nitro Compound Table 5 below shows data obtained for Examples 5a to 5e according to this invention by conducting the hydrogenation using different catalysts as the heterogeneous catalysts according to the above test protocol, but varying the amount of TDA (mixture of regioisomers in a ratio of 80% of 2,4-TDA and 20% of 2,6-TDA). The amount of catalyst was varied with respect to the amount of TDA. Hydrogenation Examples 5a to 5e were conducted with catalyst systems comprising, in addition to the heterogeneous catalysts, DNT.

TABLE 5

COMPARISON OF INITIAL REACTION RATES, CONVERSIONS
AND CHEMOSELECTIVITIES FOR CATALYST SYSTEMS
ACCORDING TO THE INVENTION AT A HIGHER
ADDITIVE CONCENTRATION

| Example | 2,4-TDA grams | 2,6-TDA grams | Catalyst System | Initial Rate $mol_{H_2}/min/g_{cat}$ | Conversion percent | Selectivity percent |
|---|---|---|---|---|---|---|
| 5a | 0.60 | 0.15 | 0.33 g Ru1<br>0.25 g DNT | 0.0067 | 97.6 | 89.4 |
| 5b | 0.60 | 0.15 | 0.30 g Ru1<br>0.002 g Ni1<br>0.25 g DNT | 0.0035 | 99.3 | 89.5 |
| 5c | 0.60 | 0.15 | 0.30 g Ru2<br>0.034 g Rh1<br>0.25 g DNT | 0.0073 | 99.5 | 83.0 |
| 5d | 0.40 | 0.10 | 0.33 g Ru1<br>0.50 g DNT | 0.0022 | 96.6 | 89.3 |
| 5e | 0.40 | 0.10 | 0.30 g Ru1<br>0.002 g Ni1<br>0.50 g DNT | 0.0053 | 96.4 | 89.7 |

The data in Table 5 show that also with high concentrations of DNT as organic nitro compound in the catalyst system according to this invention high initial reaction rates are obtained. The desired high conversions and chemoselectivities are maintained. In examples 5a to 5e the use of 2,4-dinitrotoluene as organic nitro compound according to the invention provided an additional amount of 2,4-diamino-1-methyl-cyclohexane.

The invention described herein provides a catalyst system for hydrogenating aromatic di- and polyamines to cycloaliphatic di- and polyisocyanates characterised by a unique combination of high activity, high chemoselectivity to primary amine and high diastereomer selectivity relative to conventional heterogeneous catalysts, which is highly desired in the relevant chemical industries. This combination of features provides savings in energy, raw materials, chemical waste and material recycling costs, which are of value to society and the environment.

The present invention may be embodied in other specific forms without departing from the spirit or essential attributes thereof and, accordingly, reference should be made to the appended claims, rather than to the foregoing specification, as indicating the scope of the invention.

The invention claimed is:

1. A process for hydrogenating aromatic di- and polyamines comprising the steps of:
   reacting, in a reactor, at least one aromatic amine with hydrogen in the presence of a catalytic system, wherein the catalytic system comprises at least one heterogeneous catalyst, wherein the heterogeneous catalyst comprises a metal selected from the group consisting of Cr, Mo, W, Mn, Re, Fe, Ru, Os, Co, Rh, Ir, Ni, Pd, Pt and combinations thereof, and wherein the catalyst system further comprises an organic nitro compound; and obtaining a reaction product from the reaction.

2. The process according to claim 1, wherein the aromatic amine is selected from the group consisting of o-, m-, and p-phenylenediamine, 2,3-diaminotoluene, 2,4-diaminotoluene, 2,6-diaminotoluene, 3,4-diaminotoluene, 2,3-diamino-p-xylene, 2,5-diamino-p-xylene, 2,6-diamino-p-xylene, N-methyl-o-phenylenediamine, N-ethyl-o-phenylenediamine, 4-methoxy-m-phenylenediamine, N-methyl-m-phenylenediamine, N-ethyl-m-phenylenediamine, N-isobutyl-p-phenylenediamine, N-isoamyl-p-phenylenediamine, N-cyclohexyl-p-phenylenediamine, N-benzyl-p-phenylenediamine, N-phenyl-p-phenylenediamine, N,N'-diethyl-p-phenylenediamine, N,N'-di(n-propyl)-p-phenylenediamine, N-methyl-N'-(n-propyl)-p-phenylenediamine, N-(n-butyl)-N'-benzyl-p-phenylenediamine, N,N'-dibenzyl-p-phenylenediamine, benzidine, N,N,N',N'-tetramethylbenzidine, 4,4'-oxydianiline, 4,4'-, 2,4'- and/or 2,2'-methylenedianiline, 4,4'-methylene-bis(N,N-dimethylaniline), 4,4'-methylene-bis(N-methylaniline), bis(3-methyl-4-aminophenyl)methane, 4,4'-ethylenedianiline, 2,4-diamino-N-phenylaniline, 2,4-bis(4-aminobenzyl)aniline, 1,2,4,5-tetraaminobenzene, bis(3,4-diaminophenyl)methane and combinations thereof.

3. The process according to claim 2, wherein the aromatic amine is 2,4-diaminotoluene and/or 2,6-diaminotoluene and the reaction product comprises a mixture of 2,4-diamino-1-methyl-cyclohexane and 2,6-diamino-1-methyl-cyclohexane, wherein ≤50 mol % of said diamino-1-methyl-cyclohexane reaction products are in the cis-cis-isomer configuration and ≤15 mol % of said diamino-1-methyl-cyclohexanes reaction products are in the trans-trans-isomer configuration.

4. The process according to claim 1, wherein the metal of the heterogeneous catalyst is on a support selected from the group consisting of alumina, silica, titania, ceria, carbon and combinations thereof.

5. The process according to claim 1, wherein the metal of the first heterogeneous catalyst is ruthenium, rhodium, nickel or cobalt.

6. The process according to claim 1, wherein two heterogeneous catalysts are utilized, wherein the first heterogeneous catalyst is a supported ruthenium catalyst and the second heterogeneous catalyst is comprised of rhodium on silica, rhodium on alumina, nickel on silica, nickel on alumina, cobalt on silica or cobalt on alumina.

7. The process according claim 1, wherein the organic nitro compound is selected from the group consisting of nitromethane, nitroethane, 1-nitropropane, 2-nitropropane, all isomers of nitrobutane, nitropentane and nitrohexane, 2-nitroheptane, 2-nitrooctane, nitrocyclopentane, nitrocyclohexane, 4-nitropyridine, 4-nitropiperidine, nitromethylbenzene, nitrobenzene, 4-fluoronitrobenzene, 4-chloronitrobenzene, 4-bromonitrobenzene, 2-nitroaniline, 3-nitroaniline, 4-nitroaniline, 2-nitrophenol, 3-nitrophenol, 4-nitrophenol, 1-methoxy-2-nitrobenzene, 1-methoxy-3-nitrobenzene, 1-methoxy-4-nitrobenzene, N-cyclohexylmethyl-4-nitroaniline, N-(1(4-nitrophenyl)ethyl)cyclohexaneamine, 2- and/or 4-nitrotoluene, 4-isopropylnitrobenzene, nitrostyrene, 4-nitrodiphenylmethane, 1-nitro-4-phenoxybenzene, 2,3-, 2,4-, 2,6- and 3,4-dinitrotoluene, and combinations thereof.

8. The process according to any one of the preceding claims, wherein the process is conducted in the absence of at least one of Pd and Pt.

9. The process according to claim 1, wherein the organic nitro compound is added to the reactor during the course of the reaction.

10. The process according to claim 1, wherein the reactor is a trickle bed reactor.

11. The process according to claim 1, wherein the reaction is carried out at a temperature in the range from ≥120° C. to ≤250° C.

12. The process according to claim 1, wherein the molar ratio of catalytically active metal or metals in the heterogeneous catalyst or catalysts to organic nitro compound or organic nitro compounds is in a range of ≥0.01 to ≤10.

13. The process according to claim 1, wherein the catalytic system comprises a mixture of at least two heterogeneous catalysts, wherein the first and the second heterogeneous catalyst comprise a metal selected from the group consisting of Cr, Mo, W, Mn, Re, Fe, Ru, Os, Co, Rh, Ir, Ni, Pd, Pt and combinations thereof with the further proviso that the metal selected for the second heterogeneous catalyst is different from the metal selected for the first heterogeneous catalyst.

14. The process according to claim 13, wherein the first heterogeneous catalyst and the second heterogeneous catalyst are spatially separated from each other in the reactor.

* * * * *